United States Patent [19]
Owen

[11] Patent Number: 5,196,627
[45] Date of Patent: Mar. 23, 1993

[54] ISOPARAFFIN:OLEFIN ALKYLATION PROCESS AND REACTOR APPARATUS

[75] Inventor: Hartley Owen, Belle Mead, N.J.

[73] Assignee: Mobil Oil Corporation, Fairfax, Va.

[21] Appl. No.: 796,510

[22] Filed: Nov. 21, 1991

[51] Int. Cl.$^5$ .............................................. C07L 2/62
[52] U.S. Cl. ..................... 585/723; 585/724; 585/725; 585/701; 585/921; 585/922; 585/924; 585/926
[58] Field of Search ............. 585/723, 725, 724, 701, 585/921, 922, 924, 926

[56] References Cited
U.S. PATENT DOCUMENTS

| | | | |
|---|---|---|---|
| 3,108,048 | 10/1963 | McDonald | 585/723 |
| 3,212,860 | 10/1965 | Vernon | 585/723 |
| 3,435,092 | 3/1969 | Hutson, Jr. et al. | 585/723 |
| 3,867,103 | 2/1975 | Boney et al. | 585/723 |
| 4,938,935 | 7/1990 | Audeh et al. | 423/240 |
| 4,938,936 | 7/1990 | Yan | 423/240 |
| 4,985,220 | 1/1991 | Audeh et al. | 423/240 |

OTHER PUBLICATIONS

"Alkylation of Isobutane with $C_4$ Olefins", *Ind. Eng. Chem. Res.*, 381–397 (1988).
*Handbook of Petroleum Refining Processes* 23–28 (R. A. Meyers, et al., 1986).

Primary Examiner—Asok Pal
Attorney, Agent, or Firm—Alexander J. McKillop; Dennis P. Santini; Robert B. Furr, Jr.

[57] ABSTRACT

The invention provides a substantially fail-safe HF alkylation process and reactor apparatus. The elongated reactor vessel is enclosed in a well casing and an alkylate-containing hydrocarbon layer is maintained above the hydrofluoric acid to prevent release of gaseous HF in the event of sudden depressurization. In a preferred embodiment, the hydrocarbon layer contains light hydrocarbons which vaporize upon depressurization to effect Joule-Thompson cooling of the reactor vessel. A method for storing hazardous liquids and a penetration-resistant storage tank are also disclosed.

12 Claims, 4 Drawing Sheets

ISOPARAFFIN:OLEFIN ALKYLATION PROCESS AND REACTOR APPARATUS

CROSS REFERENCE TO RELATED APPLICATIONS

This application is related by disclosure of similar subject matter to U.S. application Ser. No. 07/796,522, filed on even date herewith.

FIELD OF THE INVENTION

The present invention relates to the art of catalytic alkylation. Particularly, the invention relates to an isoparaffin:olefin alkylation process and reactor apparatus.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used hydrofluoric or sulfuric acid catalysts under relatively low temperature conditions. Acid strength is preferably maintained at 88 to 94 weight percent by the continuous addition of fresh acid and the continuous withdrawal of spent acid.

Hydrofluoric acid alkylation processes share inherent drawbacks including environmental and safety concerns, acid consumption, and sludge disposal. For a general discussion of liquid acid catalyzed isoparaffin:olefin alkylation, see the series of three articles by L. F. Albright et al., "Alkylation of Isobutane with $C_4$ Olefins", 27 Ind. Eng. Chem. Res., 381-397, (1988). For a survey of hydrofluoric acid catalyzed alkylation, see 1 *Handbook of Petroleum Refining Processes* 23-28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry used anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Examples of precautions include storing and handling HF in process equipment which is substantially impervious to HF attack under the selected process conditions. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release. U.S. Pat. Nos. 4,938,935 and 4,985,220 to Audeh and Greco, as well as U.S. Pat. No. 4,938,936 to Yan teach various methods for containing and/or neutralizing HF acid clouds following accidental releases.

Operating experience with existing HF alkylation units has proven that the likelihood of catastrophic storage tank or reactor vessel failure is remote. This invention provides an inherently safe reactor vessel and storage tank for hydrofluoric acid to further improve the safe and environmentally responsible operation of commercial hydrofluoric acid catalyzed isoparaffin:olefin alkylation process units.

SUMMARY OF THE INVENTION

The present invention provides an isoparaffin:olefin alkylation process and reactor configuration which overcomes the safety and environmental concerns relating to the handling and storage of concentrated HF.

The invention provides a process for alkylating an isoparaffin with an olefin in the presence of hydrofluoric acid comprising the steps of:

(a) providing a longitudinally extensive reaction vessel for retaining a less dense hydrocarbon phase superimposed above a lower hydrofluoric acid phase;

(b) providing a jacket surrounding and substantially concentric with said longitudinally extensive reaction vessel and flowing liquid into the annular region defined by said longitudinally extensive reaction vessel and said jacket;

(c) controlling the height of said less dense hydrocarbon phase above said more dense hydrofluoric acid phase within said longitudinally extensive reaction vessel such that the head exerted by said less dense hydrocarbon phase on said hydrofluoric acid phase is sufficient to maintain said hydrofluoric acid phase in the liquid state in the absence of externally applied pressure at operating temperature;

(d) flowing feedstock containing at least one paraffin and at least one olefin through said hydrofluoric acid phase under alkylation conditions to convert at least a portion of said feedstock to alkylate product; and (e) withdrawing hydrocarbon containing said alkylate product from an upper portion of said reaction vessel.

The invention further provides a reactor for alkylating an isoparaffin with an olefin in the presence of hydrofluoric acid comprising:

(a) a longitudinally extensive reaction vessel for retaining a less dense hydrocarbon phase superimposed above a lower hydrofluoric acid phase;

(b) a jacket surrounding and substantially concentric with said longitudinally extensive reaction vessel for maintaining a fluid within the annular region defined by said longitudinally extensive reaction vessel and said jacket;

(c) a liquid level controller for maintaining the height of said less dense hydrocarbon phase above said more dense hydrofluoric acid phase within said longitudinally extensive reaction vessel such that the head exerted by said less dense hydrocarbon phase on said hydrofluoric acid phase is sufficient to maintain said hydrofluoric acid phase in the liquid state in the absence of externally applied pressure at operating temperature;

(d) a feed distributor for introducing feedstock containing at least one paraffin and at least one olefin into said hydrofluoric acid phase under alkylation conditions to convert at least a portion of said feedstock to alkylate product; and (e) conduit for withdrawing hydrocarbon containing said alkylate product from an upper portion of said reaction vessel.

The invention provides a method for storing a volatile liquid comprising the steps of:

(a) providing a longitudinally extensive storage vessel for retaining a less dense liquid phase superimposed above a more dense volatile liquid phase;

(b) providing a jacket surrounding and substantially concentric with said longitudinally extensive storage vessel forming an annular region defined by said longitudinally extensive reaction vessel and said jacket for retaining a liquid; and (c) controlling the height of said less dense liquid phase above said more dense volatile liquid phase within said storage vessel such that the head exerted by said less dense liquid phase on said more dense volatile liquid phase is sufficient to maintain said more dense volatile liquid phase in the liquid state in the absence of externally applied pressure at storage temperature.

The invention still further provides a penetration resistant storage vessel for storing volatile liquid comprising:

(a) a longitudinally extensive storage vessel for retaining a less dense liquid phase superimposed above a more dense volatile liquid phase;

(b) a fluid-retaining jacket surrounding and substantially concentric with said longitudinally extensive reaction storage vessel forming an annular region defined by said longitudinally extensive reaction vessel and said jacket; and (c) a liquid level controller for maintaining the height of said less dense liquid phase above said more dense volatile liquid phase within said longitudinally extensive reaction vessel such that the head exerted by said less dense liquid phase on said more dense volatile liquid phase is sufficient to maintain said more dense volatile liquid phase in the liquid state in the absence of externally applied pressure at storage temperatures.

DETAILED DESCRIPTION

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include ethylene, propylene, butene-1, butene-2, isobutylene, amylene, hexene, heptene, and octene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44-56, the disclosure of which is incorporated by reference as if set forth at length herein.

The molar ratio of isoparaffin to olefin is generally from about 1:1 to about 100:1, preferably from about 1:1 to about 50:1, and more preferably from about 5:1 to about 20:1.

Isoparaffin:Olefin Alkylation Process Conditions

The conversion conditions for the process of the present invention resemble those of typical commercial hydrofluoric acid alkylation processes. The present alkylation process is suitably conducted at temperatures of from about 10° to about 100° C., preferably from about 20° to about 80° C., and more preferably below about 25° C. to avoid undesirable side reactions. Pressure is maintained to ensure a liquid phase in the alkylation reaction zone, typically falling within the range of from about 20 to about 1200 psig, and preferably are within the range of from about 50 to about 500 psig. Olefin feed rates can vary from 0.01 to 10 weight hourly space velocity (WHSV), and are preferably from about 0.05 to about 5 WHSV. Contact times for isoparaffin:olefin feed with the catalyst composition of the present invention can range from about 0.1 second to about 100 minutes, and more preferably are from about 10 seconds to about 20 minutes.

Light hydrocarbon ($C_3-$) may optionally be added to the feedstock to enhance Joule-Thompson cooling in the event of depressurization due to piping or vessel wall failure. While the head pressure exerted on the hydrofluoric acid by the hydrocarbon phase is sufficient to prevent vaporization of the hydrofluoric acid, the Joule-Thompson cooling is desirable to minimize the vapor pressure exerted by the hydrofluoric acid.

Figure 1:
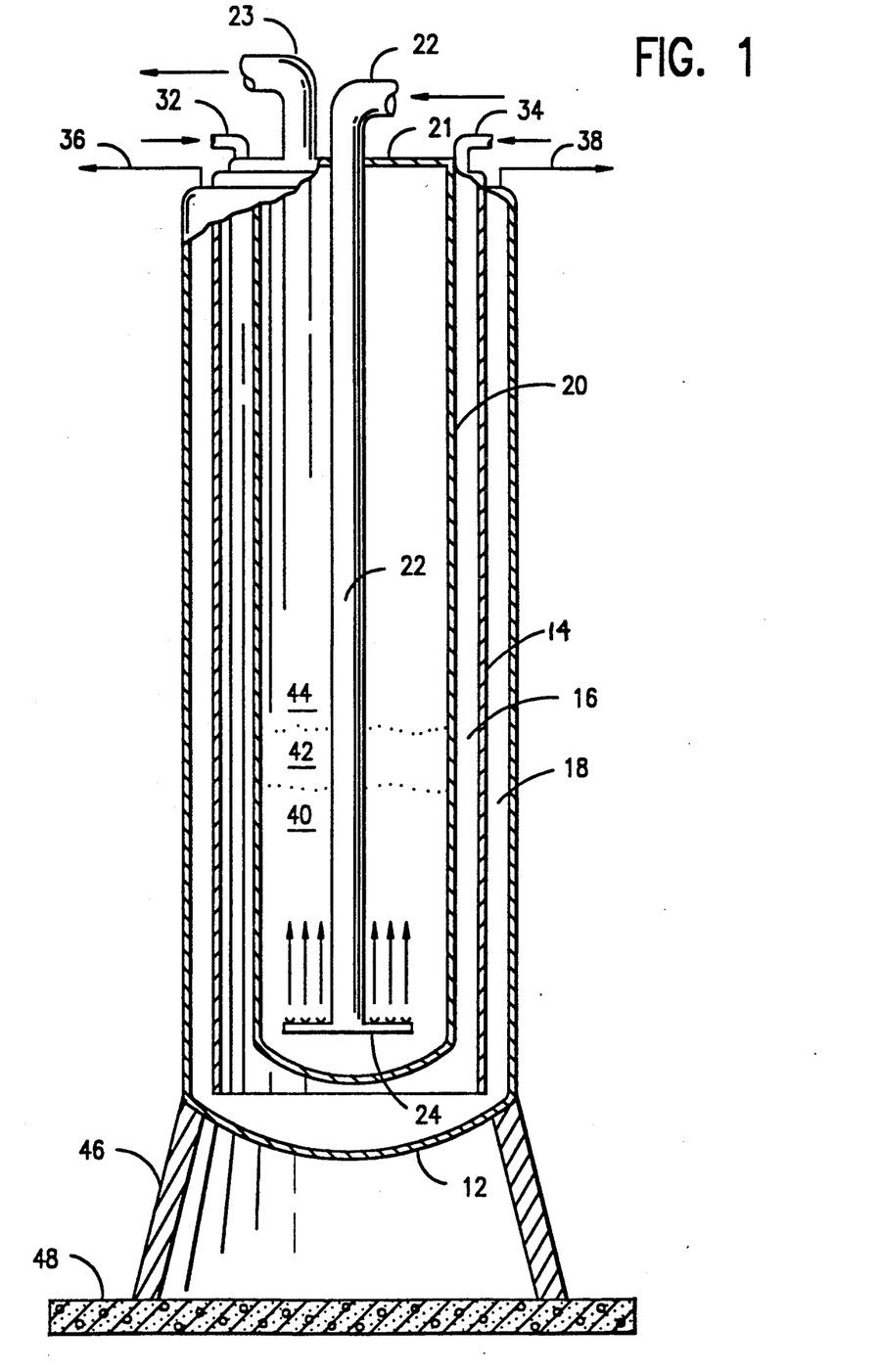
FIG. 1 is simplified schematic diagram of a first embodiment of the reactor apparatus of the invention.

FIG. 1 illustrates a simplified schematic diagram of a first embodiment of the reactor apparatus of the invention. As used herein, the term "reactor apparatus" refers to process equipment including a reactor vessel, cooling tubes or jacket, as well as the associated hydrocarbon and catalyst feed and distribution conduits.

The first embodiment shown in FIG. 1 includes an outer cylindrical shell 12, supported by structures 46 on a foundation 48, which may optionally be surrounded by a penetration-resistant jacket. The cylindrical shells described below, together with the fluid-filled heat exchange annuli, protect the reactor vessel 20 from penetration by projectiles which may be generated by an accidental explosion within the petroleum refining complex. The reactor and storage vessels of the invention may also be configured to resist intentionally applied explosive forces, for example, artillery. If the reactor apparatus must be substantially impervious to more severe impact than would likely be generated by an accidental explosion within a refining complex, a penetration-resistant jacket (not shown) may optionally surround outer cylindrical shell 12. The cylindrical shells described below, together with the fluid-filled heat exchange annuli, can easily be sized to resist the majority of intentionally applied forces. The optional penetration resistant jacket could be employed to resist, for example, penetration by an artillery shell such as a 120 mm depleted uranium projectile. The annular space between the outer cylindrical shell 12 and the optional penetration-resistant jacket may be filled with an inert material such as water, clay, or paraffin wax, or may optionally contain an acid neutralizing material such as an aqueous solution containing KOH, NaOH or acetic acid.

Heat exchange shell 14 (an open-ended elongated cylinder) is suspended inside of and positioned concentrically with outer cylindrical shell 12 to define an inner heat exchange annulus 16 and an outer heat exchange annulus 18. Reactor vessel 20 (a closed elongated cylinder) extends longitudinally and concentrically through heat exchange shell 14.

The distance between the outer surface of reactor vessel 20 and the inner surface of heat exchange shell 14 is defined as the thickness of the inner heat exchange annulus 16. Similarly, the distance between the outer surface of heat exchange shell 14 and the inner surface of the outer cylindrical shell 12 is defined as the thickness of the outer heat exchange annulus 18. Increasing the thickness of one or both annuli increases the penetration resistance of the reactor apparatus. The optimum thickness for the annuli may be determined by one skilled in the art with a minimum of trial and error. Heat exchange shell 14 retains no pressure and may be fabricated with material of the minimum thickness necessary for safe handling during construction and subsequent maintenance. Outer cylindrical shell 12, on the other hand, must be designed to retain the greater of the pressures exerted by the (a) coolant flowing the the heat exchange annuli; or (b) the operating pressure within reactor vessel 20.

Hydrocarbon feed conduit 22 extends downwardly from the top of reactor vessel 20, terminating in feed distributor 24 near the bottom of reactor vessel 20. Feed distributor 24 contains a plurality of upwardly-facing nozzles for sparging the hydrocarbon feed into a liquid acid catalyst maintained in the bottom portion of the reactor vessel.

Coolant enters the inner heat exchange annulus 16 through nozzles 32 and 34 and flows downwardly, cooling the reactor vessel 20. The coolant then flows out of the inner heat exchange annulus 16 and upwardly through outer heat exchange annulus 18 where it is withdrawn through nozzles 36 and 38.

During process operation, the reactor vessel 20 contains two substantially immiscible phases: the lower hydrofluoric acid phase 40 and the upper hydrocarbon phase 44. Hydrocarbon feed flows into the reactor vessel through feed conduit 22 and feed distributor 24 (as described above) and flows upwardly through the lower, more dense hydrofluoric acid phase. The nozzles of the feed distributor divide the hydrocarbon feed into fine droplets to maximize contact between the hydrocarbon reactants and the hydrofluoric acid as the (less dense) hydrocarbon droplets rise through the (more dense) hydrofluoric acid phase.

The rising hydrocarbon droplets and the hydrofluoric acid catalyst may form a transition phase 42 as the less dense hydrocarbons gravitationally separate from the more dense hydrofluoric acid catalyst. The location of the acid:hydrocarbon interface (or the transition zone, if formed) with respect to the total length of the reactor vessel is an essential feature of the most preferred embodiment of the process of the present invention. The weight of the column of hydrocarbon above the hydrofluoric acid must exert sufficient force upon the surface of the hydrofluoric acid to maintain the hydrofluoric acid in the liquid phase absent externally applied pressure. Thus in the most preferred embodiment, if the upper head 21 of reactor vessel 20 ruptures, or if there is a catastrophic failure in the associated piping, the Joule-Thompson cooling caused by the vaporization of $C_4-$ hydrocarbons from the upper hydrocarbon phase 44, combined with the pressure exerted upon the hydrofluoric acid by the weight of the remaining $C_5+$ alkylate hydrocarbon liquid above the hydrofluoric acid, is sufficient to prevent vaporization and release of hydrofluoric acid from the reactor vessel.

Liquid level sensors (not shown) monitor the height of the hydrocarbon/acid interface within reactor vessel 20 and control the relative charge rates of acid and hydrocarbon to maintain the necessary height of hydrocarbon above the hydrofluoric acid layer. Because hydrofluoric acid gradually deactivates during isoparaffin:olefin alkylation catalysis due to the accumulation of impurities, acid regeneration piping (not shown) continuously removes a portion of the used acid from the hydrofluoric acid layer and returns purified and/or fresh makeup acid to the lower hydrofluoric acid layer.

Hydrocarbon liquid containing both unreacted isobutane and alkylate product is withdrawn from the reactor vessel via product outlet nozzle 23 for further processing. Unreacted isobutane is separated from the hydrocarbon liquid and recycled as a constituent of the hydrocarbon feed while the alkylate product is routed to gasoline blending and storage facilities.

Figure 2:
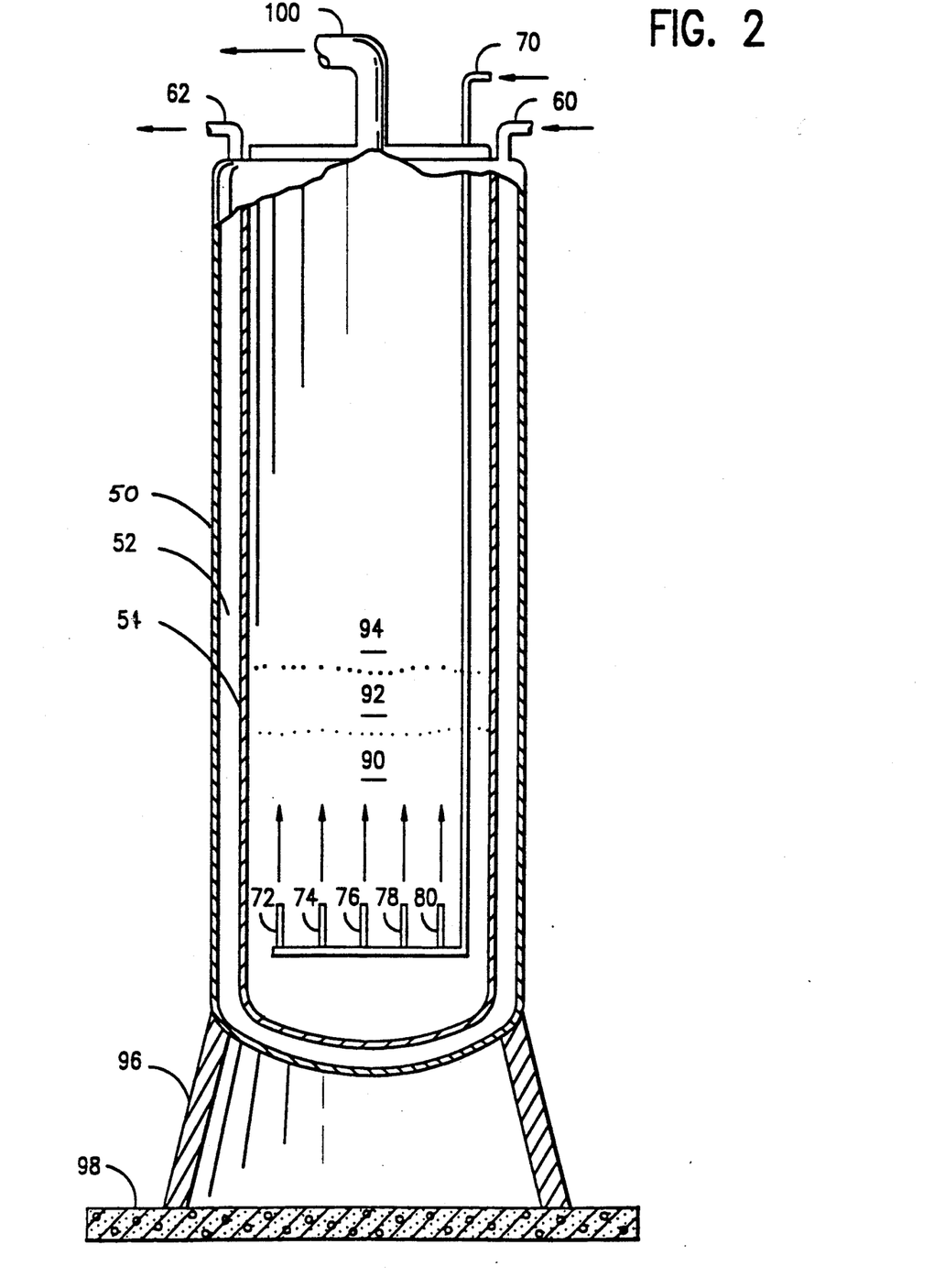
FIG. 2 is a simplified schematic diagram of a second embodiment of the reactor apparatus of the invention which maintains reaction temperature by processing a refrigerated hydrocarbon feed.

FIG. 2 illustrates a second embodiment of the reactor apparatus of the invention. Unlike the first embodiment described above, the second embodiment maintains reaction temperature by processing a refrigerated hydrocarbon feed. The feed may be chilled by any suitable technique, and is preferably chilled via autorefrigeration (Joule-Thompson cooling).

The second embodiment comprises an outer cylindrical shell 50 supported by structures 96 on a foundation 98, surrounding an annular region 52 defined by the inner surface of outer cylindrical shell 50 and the outer surface of reactor vessel 54. A fluid, for example an inert gas such as nitrogen or steam, enters the annular region 52 through inlet nozzle 60, circulates through the annular region, and is withdrawn through outlet nozzle 62. The annular space may optionally filled with an inert material such as water, clay, or paraffin wax, or may optionally contain an acid neutralizing material such as an aqueous solution containing KOH, NaOH or acetic acid.

If a fluid is circulated through the annular region, the fluid may be withdrawn and charged to a hydrofluoric acid detector to signal process unit control board alarms if an HF leak is detected. The withdrawn fluid may also be charged to a neutralization unit, for example a KOH treater.

Mixed isoparaffin:olefin feed enters the reactor vessel through line 70 which terminates in a plurality of distributor nozzles 72, 74, 76, 78, and 80 (only five are shown) positioned near the bottom of the hydrofluoric acid phase 90. The mixed hydrocarbon feed flows upwardly through the hydrofluoric acid phase, and gravitationally separates from the hydrofluoric acid phase to form a transition phase 92, and finally enters the hydrocarbon phase 94. The decanted hydrocarbon phase (containing both unreacted isobutane and alkylate product) is withdrawn from the reactor vessel via outlet nozzle 100 for further processing.

Figure 3:
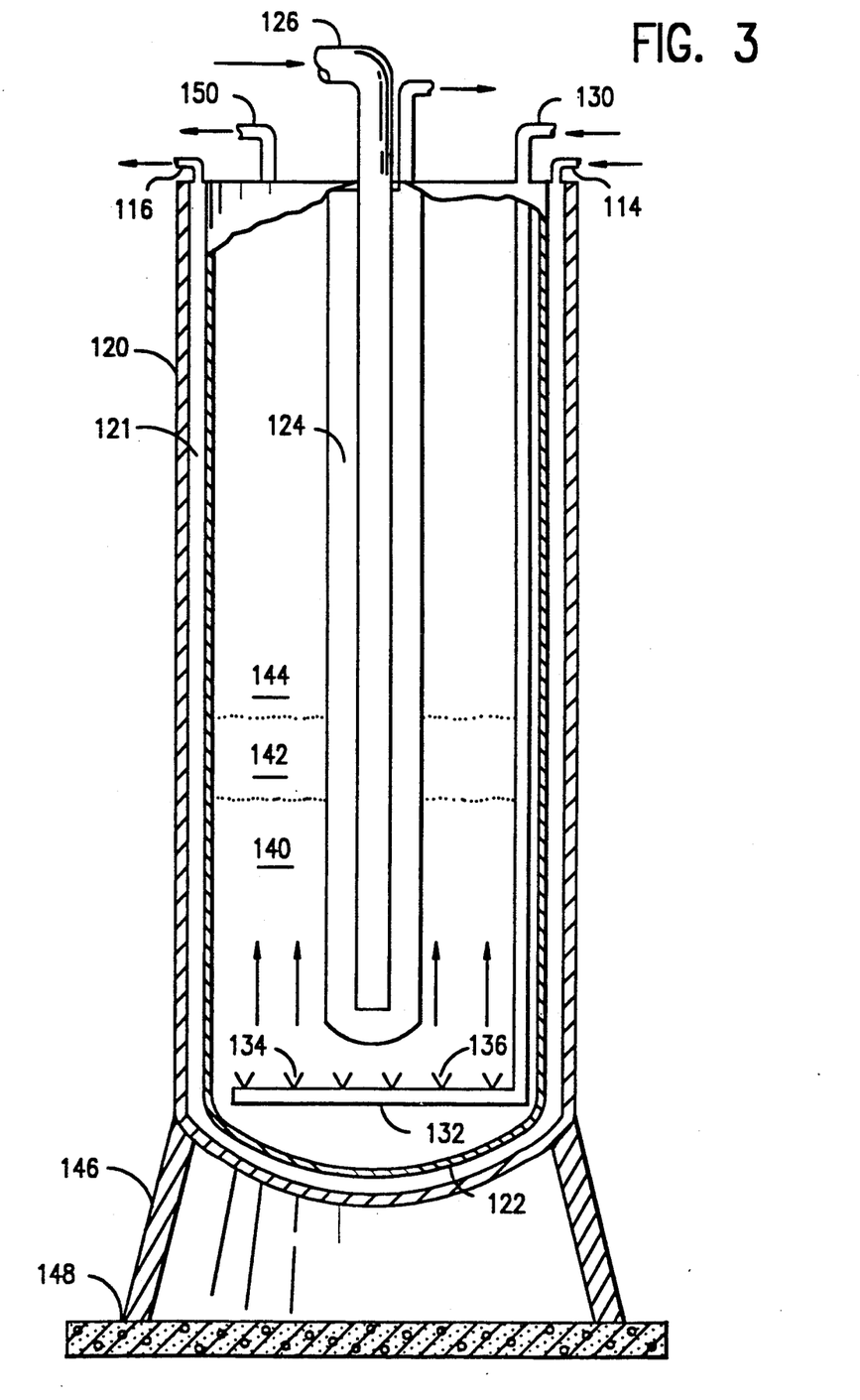
FIG. 3 is a simplified schematic diagram of a third embodiment of the reactor apparatus of the invention in which coolant is circulated through a heat exchange conduit extending longitudinally through the reactor vessel.

FIG. 3 illustrates a third embodiment of the apparatus of the invention comprising an outer cylindrical shell 120 and reactor vessel 122 supported by structures 146 on a foundation 148. The outer cylindrical shell 120 and the reactor vessel 122 together define annular region 121. An inert fluid, preferably a liquid, is circulated through annular region 121, via lines 114 and 116. Heat exchanger 124 extends longitudinally through the reactor vessel, with its bottom head preferably located just above the feed distributor 132. Coolant feed line 126 charges coolant (e.g., cooling water) to heat exchanger 124, releasing the coolant near the bottom of the heat exchanger. The coolant then flows upwardly through the annular region formed by the inner surface of heat exchanger 124 and the outer surface of coolant feed line 126.

Mixed isoparaffin:olefin feed enters the reactor vessel through line 130 which terminates in a plurality of distributor nozzles 134, 136 (only two are designated) positioned near the bottom of the hydrofluoric acid phase 140. The mixed hydrocarbon feed flows upwardly through the hydrofluoric acid phase, and gravitationally separates from the hydrofluoric acid phase to form a transition phase 142, and finally enters the hydrocarbon phase 144. The decanted hydrocarbon phase (containing both unreacted isobutane and alkylate product) is withdrawn from the reactor vessel via outlet nozzle 150 for further processing.

Figure 4:
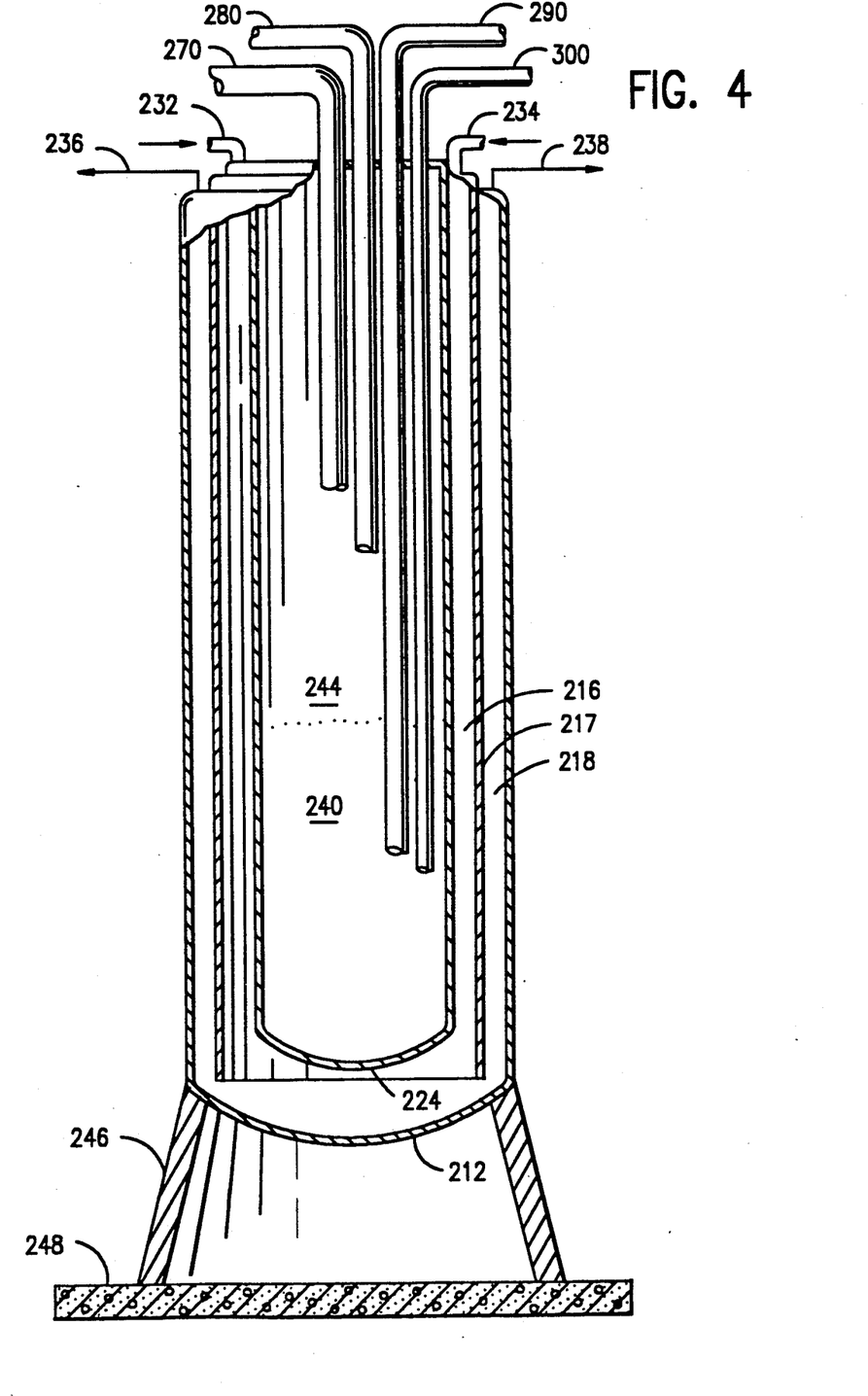
FIG. 4 is a simplified schematic diagram of an embodiment of the storage vessel of the present invention.

FIG. 4 illustrates an embodiment of the storage vessel of the present invention which finds particular utility in storing hazardous liquids. More specifically, the storage vessel is useful for retaining relatively dense liquids. The storage vessel of the invention holds the relatively dense hazardous liquid in a lower portion of a storage vessel under a blanket of substantially immiscible less dense fluid. Concentrated hydrofluoric acid is one important (albeit nonlimiting) example of such a relatively dense hazardous liquid.

Outer cylindrical shell 212 may be supported in any suitable manner in accordance with the applicable pressure vessel code, for example by skirt 246 and concrete pad 248.

The cylindrical shells described below, together with the fluid-filled heat exchange annuli, protect the storage vessel 224 from penetration by projectiles. The storage vessel is surrounded by at least one fluid-filled annular region, and may optionally be surrounded by two or more annular regions. The annular region between the outer cylindrical shell 212 and the optional penetration-resistant jacket may be filled with an inert material such as water, clay, or paraffin wax, or may optionally contain an acid neutralizing material such as an aqueous solution containing KOH, NaOH or acetic acid.

Cylindrical sleeve 217 (an open-ended elongated cylinder) may optionally be employed to provide two concentric annuli for circulating fluid substantially longitudinally in contact with storage vessel 224. Cylindrical sleeve 217 may be suspended inside of and positioned concentrically with outer cylindrical shell 212 to define an inner annulus 216 and an outer annulus 218. Storage vessel 224 (a closed elongated cylinder) is positioned within and substantially concentric with outer shell 212.

The distance between the outer surface of storage vessel 224 and the inner surface of cylindrical sleeve 217 defines the thickness of the inner annulus 216. Similarly, the distance between the outer surface of cylindrical sleeve 217 and the inner surface of the outer cylindrical shell 212 is defined as the thickness of the outer annulus 218. Increasing the thickness of one or both annuli increases the penetration resistance of the reactor apparatus. The optimum thickness for the annulus (or, optionally, annuli) may be determined by one skilled in the art with a minimum of trial and error.

The stored product resides in a lower phase 240 within storage vessel 224. While hydrofluoric acid and hydrocarbon are used to describe the present invention, it is to be understood that any pair of substantially immiscible fluids may be used in the storage method and apparatus of the invention if the hazardous fluid is the more dense of the two fluids.

Transfer conduits 270 and 280 extend downwardly from the top of storage vessel 224, terminating in the less dense upper (hydrocarbon) phase 244. Transfer conduits 290 and 300 extend downwardly from the top of storage vessel 224 into the lower (hydrofluoric acid) phase 240. The lower transfer conduits 290 and 300 charge and withdraw the stored fluid (hydrofluoric acid), while the upper transfer conduits 270 and 280 charge and withdraw the less dense fluid (hydrocarbon).

The annular fluid enters the inner annulus 216 through nozzles 232 and 234 and flows downwardly. The fluid then flows out of the inner annulus 216 and upwardly through outer annulus 218 where it is withdrawn through nozzles 236 and 238.

The location of the acid:hydrocarbon interface (or the transition zone, if formed) with respect to the total length of the storage vessel is an essential feature of the most preferred embodiment of the storage method of the present invention. The weight of the column of the less dense fluid (hydrocarbon) above the more dense stored fluid (hydrofluoric acid) must exert sufficient force upon the surface of the hydrofluoric acid to maintain the hydrofluoric acid in the liquid phase absent externally applied pressure. Mixed hydrocarbons containing a substantial proportion of $C_4-$ hydrocarbons are particularly preferred for the upper less dense fluid to effect Joule-Thompson cooling in the event of piping or vessel failure. Thus in the most preferred embodiment, if the upper head of storage vessel 224 ruptures, or if there is a catastrophic failure in the associated piping, the Joule-Thompson cooling caused by the vaporization of light hydrocarbons from the upper hydrocarbon phase 244, combined with the pressure exerted upon the hydrofluoric acid by the weight of the remaining $C_5+$ alkylate hydrocarbon liquid above the hydrofluoric acid, is sufficient to prevent vaporization and release of hydrofluoric acid from the storage vessel.

Liquid level sensors (not shown) monitor the height of the hydrocarbon/acid interface within reactor vessel 224 and control the relative charge rates of acid and hydrocarbon to maintain the necessary height of hydrocarbon above the hydrofluoric acid layer.

Changes and modifications in the specifically described embodiments can be carried out without departing from the scope of the invention which is intended to be limited only by the scope of the appended claims.

What is claimed is:

1. A process for alkylating an isoparaffin with an olefin in the presence of hydrofluoric acid comprising the steps of:
   (a) providing a longitudinally extensive reaction vessel for retaining a less dense hydrocarbon phase superimposed above a lower hydrofluoric acid phase;
   (b) providing a jacket surrounding and substantially concentric with said longitudinally extensive reaction vessel and flowing liquid into the annular region defined by said longitudinally extensive reaction vessel and said jacket;

(c) controlling the height of said less dense hydrocarbon phase above said more dense hydrofluoric acid phase within said longitudinally extensive reaction vessel such that the head exerted by said less dense hydrocarbon phase on said hydrofluoric acid phase is sufficient to maintain said hydrofluoric acid phase in the liquid state in the absence of externally applied pressure at operating temperature;

(d) flowing feedstock containing at least one paraffin and at least one olefin through said hydrofluoric acid phase under alkylation conditions to convert at least a portion of said feedstock to alkylate product; and (e) withdrawing hydrocarbon containing said alkylate product from an upper portion of said reaction vessel.

2. The process of claim 1 further comprising controlling the $C_4-$ composition of said hydrocarbon phase such that said hydrofluoric acid remains in the liquid phase upon loss of externally applied pressure.

3. The process of claim 2 further comprising cooling said hydrofluoric acid by vaporizing $C_4-$ hydrocarbons.

4. The process of claim further comprising flowing coolant through a cylindrical jacket surrounding and substantially concentric with said longitudinally extensive vessel.

5. The process of claim 1 further comprising providing a material which is substantially inert to concentrated hydrofluoric acid in an annular region defined by a cylindrical jacket surrounding and substantially concentric with said said longitudinally extensive vessel.

6. The process of claim 1 further comprising providing a material selected from the group consisting of water, clay and paraffin wax in an annular region defined by a cylindrical jacket surrounding and substantially concentric with said longitudinally extensive vessel.

7. The process of claim 1 further comprising providing a hydrofluoric acid neutralizing material in an annular region defined by a cylindrical jacket surrounding and substantially concentric with said longitudinally extensive vessel.

8. The process of claim 7 wherein said hydrofluoric acid neutralizing material comprises an aqueous solution containing KOH, NaOH or acetic acid.

9. The process of claim 1 further comprising flowing coolant through a heat exchange conduit immersed in said hydrocarbon phase.

10. The process of claim 1 further comprising flowing coolant through a heat exchange conduit immersed in said hydrofluoric acid phase.

11. The process of claim 1 further comprising providing sufficient liquid thickness within said annular region to resist penetration by a projectile.

12. The process of claim 11 further comprising providing sufficient liquid thickness within said annular region to resist penetration by a projectile generated by an accidental explosion.

* * * * *

UNITED STATES PATENT AND TRADEMARK OFFICE
CERTIFICATE OF CORRECTION

PATENT NO. : 5,196,627
DATED : March 23, 1993
INVENTOR(S) : Hartley Owen It is certified that error appears in the above-identified patent and that said Letters Patent is hereby corrected as shown below:

Col. 9, line 27, "of claim" should read --of claim 1--

Signed and Sealed this

Third Day of May, 1994

Attest:

BRUCE LEHMAN

Attesting Officer    Commissioner of Patents and Trademarks